US008063151B2

(12) United States Patent
Pacetti (10) Patent No.: US 8,063,151 B2
(45) Date of Patent: Nov. 22, 2011

(54) METHODS FOR MANUFACTURING COPOLYMERS HAVING 1-METHYL-2-METHOXYETHYL MOIETIES AND USE OF SAME (75) Inventor: Stephen Pacetti, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 566 days.

(21) Appl. No.: 11/942,707

(22) Filed: Nov. 19, 2007

(65) Prior Publication Data
US 2008/0146696 A1 Jun. 19, 2008

Related U.S. Application Data (60) Provisional application No. 60/866,800, filed on Nov. 21, 2006, provisional application No. 60/866,802, filed on Nov. 21, 2006, provisional application No. 60/866,804, filed on Nov. 21, 2006, provisional application No. 60/866,805, filed on Nov. 21, 2006, provisional application No. 60/866,798, filed on Nov. 21, 2006, provisional application No. 60/866,797, filed on Nov. 21, 2006, provisional application No. 60/866,796, filed on Nov. 21, 2006, provisional application No. 60/866,792, filed on Nov. 21, 2006.

(51) Int. Cl.
C08F 18/00 (2006.01)
C08F 8/14 (2006.01)
C08C 19/00 (2006.01)

(52) U.S. Cl. .............. 525/330.1; 525/330.6; 525/384; 525/385; 523/113; 526/320

(58) Field of Classification Search ............ 523/113; 526/319, 320, 329, 329.6, 329.7, 328.5, 330; 525/330.1, 330.6, 384, 385
See application file for complete search history.

(56) References Cited

U.S. PATENT DOCUMENTS

| 4,931,287 | A | 6/1990 | Bae et al. |
| 5,019,096 | A | 5/1991 | Fox, Jr. et al. |
| 5,155,252 | A | 10/1992 | Yamamoto et al. |
| 5,163,952 | A | 11/1992 | Froix |
| 5,258,020 | A | 11/1993 | Froix |
| 5,607,467 | A | 3/1997 | Froix |
| 5,616,338 | A | 4/1997 | Fox, Jr. et al. |
| 5,674,242 | A | 10/1997 | Phan et al. |
| 5,723,219 | A | 3/1998 | Kolluri et al. |
| 5,824,049 | A | 10/1998 | Ragheb et al. |
| 5,873,904 | A | 2/1999 | Ragheb et al. |
| 5,879,713 | A | 3/1999 | Roth et al. |
| 5,932,299 | A | 8/1999 | Katoot |
| 5,962,138 | A | 10/1999 | Kolluri et al. |
| 5,997,517 | A | 12/1999 | Whitbourne |
| 6,096,070 | A | 8/2000 | Ragheb et al. |
| 6,110,483 | A | 8/2000 | Whitbourne et al. |
| 6,143,354 | A | 11/2000 | Koulik et al. |
| 6,159,978 | A | 12/2000 | Myers et al. |
| 6,180,632 | B1 | 1/2001 | Myers et al. |
| 6,214,901 | B1 | 4/2001 | Chudzik et al. |
| 6,245,760 | B1 | 6/2001 | He et al. |
| 6,248,129 | B1 | 6/2001 | Froix |
| 6,258,371 | B1 | 7/2001 | Koulik et al. |
| 6,262,034 | B1 | 7/2001 | Mathiowitz et al. |
| 6,270,788 | B1 | 8/2001 | Koulik et al. |
| 6,277,449 | B1 | 8/2001 | Kolluri et al. |
| 6,299,604 | B1 | 10/2001 | Ragheb et al. |
| 6,306,176 | B1 | 10/2001 | Whitbourne |
| 6,344,035 | B1 | 2/2002 | Chudzik et al. |
| 6,383,509 | B1 | 5/2002 | Donovan et al. |
| 6,387,379 | B1 | 5/2002 | Goldberg et al. |
| 6,475,779 | B2 | 11/2002 | Mathiowitz et al. |
| 6,482,834 | B2 | 11/2002 | Spada et al. |
| 6,524,347 | B1 | 2/2003 | Myers et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,613,432 | B2 | 9/2003 | Zamora et al. |
| 6,620,617 | B2 | 9/2003 | Mathiowitz et al. |
| 6,663,662 | B2 | 12/2003 | Pacetti et al. |
| 6,730,064 | B2 | 5/2004 | Ragheb et al. |
| 6,776,796 | B2 | 8/2004 | Falotico et al. |
| 6,790,228 | B2 | 9/2004 | Hossainy et al. |
| 6,890,583 | B2 | 5/2005 | Chudzik et al. |
| 7,005,137 | B1 | 2/2006 | Hossainy et al. |
| 7,008,667 | B2 | 3/2006 | Chudzik et al. |
| 7,077,859 | B2 | 7/2006 | Sirhan et al. |
| 7,094,256 | B1 | 8/2006 | Shah et al. |
| 7,217,426 | B1 | 5/2007 | Hossainy |
| 7,247,313 | B2 | 7/2007 | Roorda et al. |
| 7,396,539 | B1 | 7/2008 | Hossainy et al. |
| 7,560,492 | B1 | 7/2009 | Claude et al. |
| 7,563,454 | B1 | 7/2009 | Pacetti |
| 7,713,541 | B1 | 5/2010 | Pacetti et al. |
| 2001/0007083 | A1 | 7/2001 | Roorda |

(Continued)

OTHER PUBLICATIONS

U.S. Appl. No. 11/376,348, filed Feb. 26, 2003, Ding et al.
Hunag et al., "Synthesis and Characterization of Self-Assembling Block Copolymers Containing Bioadhesive End Groups", Biomacromolecules 3, pp. 397-406 (2002).
Kocakulak et al., "Investigation of Blood Compatibility of PMEA Coated Extracorporeal Circuits", J. of Bioactive and Compatible Polymers vol. 17, pp. 343-356 (2002).
Lee et al., "Synthesis and Gelation of DOPA-Modified Poly(ethylene glycol) Hydrogels", Biomacromolecules 3, pp. 1038-1047 (2002).

(Continued)

Primary Examiner — Vasu Jagannathan
Assistant Examiner — Hannah Pak
(74) Attorney, Agent, or Firm — Squire, Sanders & Dempsey (US) LLP (57) ABSTRACT The copolymers include a hydrophobic monomer and an acryloyl or methacryloyl ester of a propylene glycol monomethyl ether, also referred to as 1-methyl-2-methoxyethyl acrylate ("MMOEA"). The combination of the hydrophobic monomer and the MMOEA monomer advantageously provides desired mechanical strength, biocompatibility, and drug permeability in the copolymers. The copolymers can advantageously be used on medical devices.

16 Claims, 2 Drawing Sheets

U.S. PATENT DOCUMENTS

| | | |
|---|---|---|
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2006/0216326 A1* | 9/2006 | Pacetti .................. 424/426 |
| 2008/0118541 A1 | 5/2008 | Pacetti |
| 2008/0124450 A1 | 5/2008 | Pacetti |
| 2008/0125514 A1 | 5/2008 | Pacetti |
| 2008/0125560 A1* | 5/2008 | Pacetti .................. 526/330 |
| 2008/0139746 A1 | 6/2008 | Pacetti |
| 2008/0146696 A1 | 6/2008 | Pacetti |
| 2008/0147178 A1 | 6/2008 | Pacetti et al. |
| 2008/0153923 A1 | 6/2008 | Pacetti |

OTHER PUBLICATIONS

Tanaka et al., "Blood compatible aspects of poly(2-methoxyethylacrylate) (PMEA)-relationship between protein adsorption and platelet adhesion on PMEA surface", Biomaterials 21, pp. 1471-1481 (2000).

Trollsas et al., "Hyperbranched Poly(ε-caprolactone) Derived from Interinsically Branched AB$_2$ Macromonomers", Macromolecules 31, p. 4390-4395 (1998).

* cited by examiner

METHODS FOR MANUFACTURING COPOLYMERS HAVING 1-METHYL-2-METHOXYETHYL MOIETIES AND USE OF SAME

CROSS-REFERENCE TO RELATED APPLICATIONS

This application claims the benefit of U.S. Provisional Patent Applications Nos. 60/866,800, 60/866,802, 60/866,804, 60/866,805 60/866,798, 60/866,797, 60/866,796, 60/866,792, all of which were filed on Nov. 21, 2006, and all of which are hereby incorporated by reference in their entirety. This application is related to co-pending U.S. patent application Ser. No. 11/942,695, entitled "Copolymers Having Zwitterionic Moieties and Dihydroxyphenyl Moieties and Medical Devices Coated with the Copolymers", co-pending U.S. patent application Ser. No. 11/942,704, entitled "Methods of Manufacturing Copolymers with Zwitterionic Moieties and Dihydroxyphenyl Moieties and Use of Same", co-pending U.S. patent application Ser. No. 11/942,693, entitled "Zwitterionic Copolymers, Method of Making and Use on Medical Devices", co-pending U.S. patent application Ser. No. 11/942,705, entitled "Amino Acid Mimetic Copolymers and Medical Devices Coated with the Copolymers", co-pending U.S. patent application Ser. No. 11/942,696, entitled "Methods for Manufacturing Amino Acid Mimetic Copolymers and Use of Same", co-pending U.S. patent application Ser. No. 11/942,700, entitled "Copolymers Having 1-Methyl-2-Methoxyethyl Moieties", all of which were filed on Nov. 19, 2007, and all of which are hereby incorporated by reference in their entirety. Co-pending U.S. patent application Ser. No. 11/939,512, filed Nov. 13, 2007, and co-pending application Ser. No. 11/562,338, filed Nov. 21, 2006 are hereby incorporated by reference in their entirety.

BACKGROUND OF THE INVENTION

1. The Field of the Invention

Embodiments of the invention relate to methods for manufacturing polymeric coatings for implantable medical devices. More particularly, embodiments of the invention relate to methods for manufacturing copolymers that include a 1-methyl-2-methoxyethyl moiety and methods for using the polymers on medical devices.

2. The Related Technology

Implantable medical devices, including stents, can be coated with polymers to give the implantable device beneficial properties when used in living tissue. Implant coatings, particularly stent coatings, typically need to simultaneously fulfill many criteria. Examples of desirable properties for implant coating properties include: adhesion to the implant (e.g., adhesion to stent struts) to prevent delamination; adequate elongation to accommodate implant deformation without buckling or cracking; sufficient hardness to withstand crimping operations without excessive damage; sterilizability; ability to control the release rate of a drug; biocompatibility including hemocompatibility and chronic vascular tissue compatibility; in the case of durable or permanent coatings, the polymer needs to be sufficiently biostable to avoid biocompatibility concerns; processability (e.g. production of stent coatings that are microns thick); reproducible and feasible polymer synthesis; and an adequately defined regulatory path.

Many methacrylate polymers exhibit several of the forgoing properties. However, most, if not all, methacrylate homopolymers lack a desired property or a combination of desired properties. For example, homopolymers of methyl methacrylate and ethyl methacrylate are too brittle. Homopolymers of n-butyl methacrylate (PBMA) are typically too hydrophobic for adequate drug elution (water absorption is only 0.4%).

Recently, efforts have been made to copolymerize methacrylate polymers with other monomers to achieve a copolymer that has the benefits of known methacrylate homopolymers and overcomes their deficiencies. The challenge with developing novel methacrylate copolymers has been achieving the desired mechanical properties while maintaining biocompatibility and useful drug permeability. Good biocompatibility is required for patient safety, device efficacy and for obtaining regulatory approval to use the polymer on an implantable medical device.

SUMMARY OF THE INVENTION

Embodiments of the invention relate to methods of manufacturing polymer coatings that include a hydrophobic monomer and a 1-methyl-2-methoxyethyl acrylate monomer ("MMOEA") or a 1-methyl-2-methoxyethyl methacrylate monomer ("MMOEM"). The copolymers manufactured according to the methods of the invention are biocompatible and suitable for use as coatings on implantable medical devices. In an exemplary embodiment, the copolymer of the invention has the following formula.

In the foregoing formula, m is in a range from about 0.1 to about 0.995, n is in a range from 0.005 to 0.9, and $R_1$ is a straight chain, branched, unsaturated, or cyclic hydrocarbon having one to sixteen carbon atoms, $R_2$ and $R_3$ are independently a methyl or a hydrogen. The combination of a hydrophobic monomer and the MMOEA monomer gives the copolymers of the invention good mechanical properties and useful drug permeability. The polymer coating can be thermoplastic without crosslinking, which is beneficial for the elongation properties of the coating.

These and other advantages and features of the invention will become more fully apparent from the following description and appended claims, or may be learned by the practice of the invention as set forth hereinafter.

BRIEF DESCRIPTION OF THE DRAWINGS

To further clarify the above and other advantages and features of the invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF EMBODIMENTS OF THE INVENTION

I. Copolymers

Embodiments of the invention relate to copolymers suitable for use on implantable medical devices. The copolymers include a hydrophobic monomer and an acryloyl or methacryloyl ester of a propylene glycol monomethyl ether, also referred to as 1-methyl-2-methoxyethyl acrylate ("MMOEA"). For purposes of this invention, the term "acrylate monomer" includes, but is not limited to, methacrylates and acrylates.

The combination of the hydrophobic monomer and the MMOEA monomer advantageously provides desired mechanical strength, biocompatibility, and drug permeability in the copolymers of the invention.

The hydrophobic monomer is an acrylate monomer that includes hydrophobic groups attached through an ester linkage. The hydrophobic group can be a straight chained, branched, unsaturated, or cyclic hydrocarbon. The hydrophobic group is typically selected to give the copolymer a suitable water absorption, glass transition temperature, and mechanical strength without cross-linking.

Examples of suitable hydrophobic monomers include, but are not limited to, methyl methacrylate, ethyl methacrylate, n-propyl methacrylate, isopropyl methacrylate, isobutyl methacrylate, sec-butyl methacrylate, 2-ethyl-hexyl methacrylate, n-hexyl methacrylate, cyclohexyl methacrylate, n-hexyl methacrylate, isobornyl methacrylate, trimethylcyclohexyl methacrylate, combinations of these, and the like.

The MMEOA monomer is selected to increase water adsorption without adversely affecting the $T_g$ of the polymer coating. The MMEOA monomer increases the water adsorption of the polymer coating because of the moderately polar groups in the side chain. The MMEOA monomer can be an acrylate or a methacrylate. The chemical structure of 1-methyl-2-methoxyethyl methacrylate (MMEOM) is:

The alkoxy structure of the 1-methoxy-2-ethoxyethyl side group confers a degree of hydrophilicity that can be used to vary the water swelling property of the polymer. Varying the water swelling varies the drug permeability of the polymer coating.

As mentioned, the MMEOA monomer is copolymerized with a hydrophobic monomer. In one embodiment, the copolymer has the formula:

In the foregoing formula, the ratio of MMEOA monomer "n" to hydrophobic monomer "m" is selected to yield a copolymer with sufficient mechanical strength for use as a coating on an implantable medical device. In an embodiment, the concentration of MMEOA monomer is in a range from 10% to 99% and the concentration of hydrophobic monomer is in a range from 1% to 90%. The copolymer can be tuned by adjusting the specific monomer ratio to achieve a desired mechanical strength and elongation. Unless otherwise stated, the monomers shown in the chemical formula above and other chemical formulas herein can be in any order within the copolymer molecule and the monomer linkages shown in the chemical formulas only represent that the monomers are part of the same copolymer molecule. Furthermore, unless otherwise stated, the polymeric molecules can include monomers other than those shown in the chemical formulas.

In one embodiment, the hydrophobic monomer is selected to yield a thermoplastic copolymer that is substantially free of cross-linking. While cross-linking can prevent excessive water swelling, cross-linking can be disadvantageous because it limits elongation, which leads to cracking of the polymer coating. Another benefit of a thermoplastic system is that it is simple to process compared to thermoset polymers.

The copolymers of the invention can also be made mechanically robust by increasing the copolymer's molecular weight. The molecular weight of the copolymer can be increased as much as possible so long as processability is not compromised. A high molecular weight yields a higher ultimate elongation for the polymer, which improves coating integrity. For a thermoplastic polymer, high molecular weight typically yields better mechanical properties.

Another advantage of the MMOEA monomer of the invention is its biocompatibility. As shown in the chemical structure, the side group of MMOEA has the smallest PEG-type group possible, a single methoxyethyl group. PEG is known for its non-fouling or protein repelling properties.

Studies on monomers analogous to MMOEA illustrate the biocompatibility of MMOEA in living tissue. For example, 2-methoxyethyl acrylate (MEA) has been extensively studied for blood contacting applications. Tanaka et al. compared the thrombogenicity of poly(2-methoxyethyl acrylate) (PMEA), poly(2-hydroxyethyl methacrylate) (PHEMA), poly(2-hydroxyethyl acrylate) (PHEA), and other alkyl methacrylates (Tanaka M., et al., Biomaterials 21 (2000) 1471-1481). Several measures of in vitro hemocompatibility, including human platelet adhesion, changes in platelet morphology, total adsorbed protein from human plasma, amount of adsorbed BSA, adsorbed human fibrinogen, and changes in protein conformation by circular dichroism were measured. In the graphs below are data showing the number of platelets adhered and the total amount of plasma protein adsorbed onto the polymers in vitro.

Figure 2:
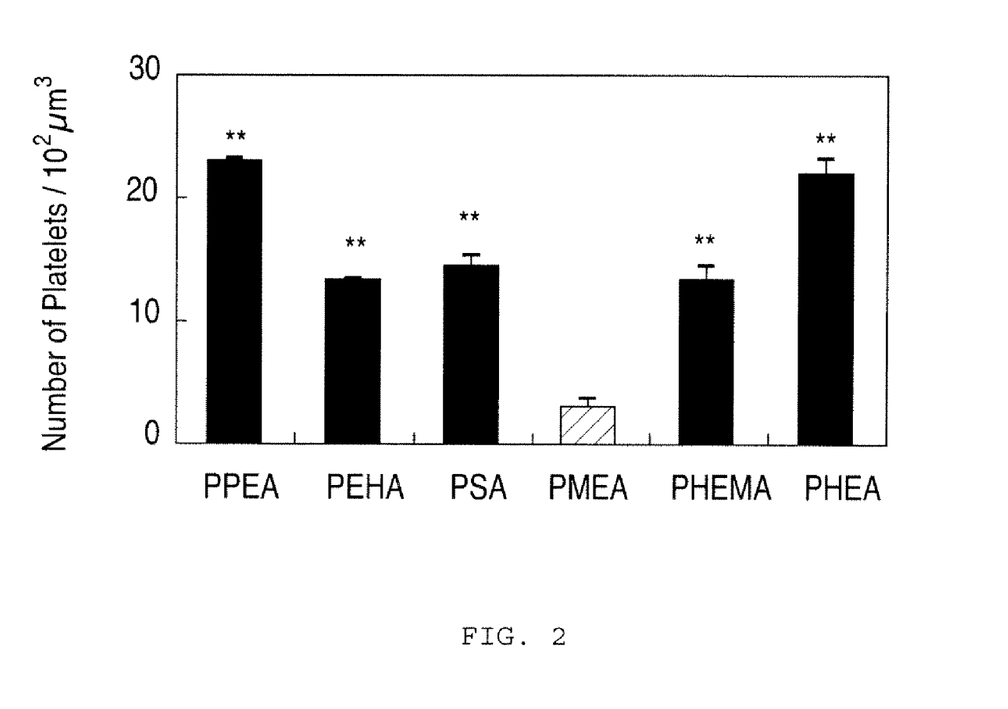
FIG. 2 shows the number of platelets adhered to the surface of several acrylate and methacrylate polymers.
Figure 3:
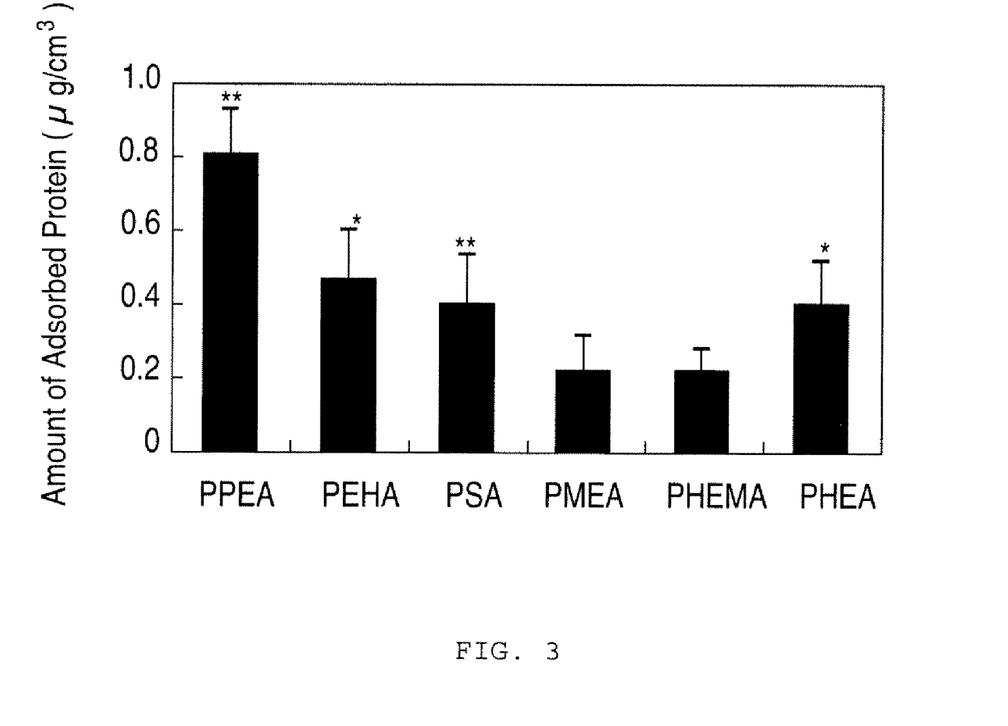
FIG. 3 shows the total amount of protein from human plasma absorbed onto several acrylate and methacrylate polymers.

In FIG. 2, the number of platelets adhered to the surface of the indicated polymethacrylates is shown. In FIG. 3, the total amount of protein from human plasma adsorbed onto the same polymers is shown. In the figures:

PMEA is poly(2-methoxyethyl acrylate)
PHEA is poly(2-hydroxyethyl acrylate)
PEA is poly(ethyl acrylate)
PEHA is poly(2-ethylhexyl acrylate)
PPEA is poly(2-phenoxyethyl acrylate) and
PHEMA is poly(2-hydroxyethylmethacrylate)

As can be seen, the PMEA coating is the most hemocompatible of the polymers tested. Kocakular, et al., investigated the blood compatibility of PMEA coated extracorporeal circuits (Kocakular, M., et al., J Bioactive and Compatible Polymers, Vol. 17, September 2002, p. 343). Hollow fiber oxygenators coated with PMEA were evaluated during twenty clinical procedures requiring cardiopulmonary bypass. The operations were compared to twenty operations with uncoated hollow fiber oxygenators. PMEA coatings were found to reduce both platelet adhesion and fibrinogen/albumin absorption. A coating of PEMA, known as the X Coating®, is used in eh CAPIOX RX blood oxygenator sold by Terumo.

Another benefit of MMOEA is the benign nature of its hydrolysis product. The ester bond in MMOEA can potentially hydrolyze in vivo to form 1-methoxy-2-propanol, which is a solvent commonly known as DOWANOL PM.

The ester bond in a 1-methyl-2-methoxyethyl moiety ("MMOE") is alpha to a tertiary carbon in the polymer backbone. Consequently, hydrolysis is sterically hindered, making hydrolysis unlikely. However, for a permanent medical implant, some hydrolysis could be possible over an extended period of time. If hydrolysis occurs, the 1-methoxy-2-propanol by product is advantageously benign. 1-methoxy-2-propanol when used as a solvent is known to be biocompatible.

1-methoxy-2-propanol is also very similar to 2-ethoxyethanol and 2-methoxyethanol in structure. Although these compounds are known to be teratogens, the toxicity of 1-methoxy-2-propanol is surprisingly in a range more similar to ethanol. A summary of the toxicity of these solvents is shown in Table 1.

TABLE 1

Toxicity Properties of Alkoxyalcohols Compared to Ethanol

| Compound | Hazard Rating | (TLV/TWA) ppm | Oral-mouse LD50 (mg/kg) |
|---|---|---|---|
| 2-ethoxyethanol | teratogen | 5 | 2451 |
| 2-methoxyethanol | teratogen | 5 | 2560 |
| 1-methoxy-2-propanol | irritant | 100 | 11700 |
| ethanol | irritant | 1000 | 3450 |

Thus, the MMEOA monomer advantageously includes an alkoxy group, which is moderately hydrophilic, and useful for tuning the drug permeability, and mechanical robustness of the copolymer. However, in contrast to 2-ethoxyethanol and 2-methoxyethanol, the toxicity of 1-methoxy-2-propanol is in a range that is similar to Ethanol. Consequently, the MMEOA monomers of the invention can have the desired hydrophilicity and biocompatibility and are particularly suited for polymeric coatings used on permanent implantable devices.

II. Methods of Manufacturing Copolymers

The method of manufacturing the copolymers of the invention generally includes selecting or forming an MMEOA monomer and reacting the MMEOA monomer with a hydrophobic monomer to form a copolymer that is suitable for coating implantable medical devices. By varying the ratio of the hydrophobic monomer to the polar monomer, the properties of the copolymer may be tuned. In an exemplary embodiment, the reaction mixture includes about 10% to about 99.5% of a hydrophobic monomer and about 0.5% to about 90% of a MMEOA monomer, based on the total moles of monomer in the reaction mixture. The type and ratio of monomers is selected to yield a copolymer that is biocompatible and mechanically robust.

The copolymers can be synthesized using free radical polymerization, cationic polymerization, anionic polymerization, atom transfer radical polymerization, iniferter polymerization, or another suitable reaction technique. Free radical polymerization can be carried out in a solvent using an initiator. Examples of solvents suitable for carrying out the polymerization reaction include alcoholic solvents, such as, but not limited to, methanol, ethanol, and isopropyl alcohol. Examples of suitable initiators for carrying out the polymerization reaction include peroxides, such as, but not limited to, benzoyl peroxide, and azo compounds. A specific example of a suitable initiator is 2,2'-azo-bis(2-methylpropionitrile). Those skilled in the art are familiar with the conditions for carrying out the foregoing polymerization reactions and other similar polymerization reactions suitable for yielding the copolymers of the invention.

An alternate path to synthesizing the polymer includes copolymerizing a functional acrylate monomer and one or more hydrophobic monomers to yield a copolymer and then modifying the copolymer to include the MMOE group. In one embodiment, a functional methacrylate monomer and a hydrophobic monomer are reacted to yield the following copolymer.

The polymerization of this polymer can be carried out using the polymerization techniques described above. Thereafter, 1-methoxy-2-propanol is coupled to the carboxy groups of the methacrylic acid. Several coupling chemistries are possible including conversion to the acid chloride or use of carbodiimides. A particularly facile technique uses dicyclohexyl carbodiimide (DCC) and 4-(dimethylamino)pyridinium (DPTS) as described in M. Trollsas, J. Hedrick, Macromolecules 1998, 31, 4390-4395.

Yet another technique for synthesizing the MMEOA including copolymers begins with the homopolymer of the hydrophobic monomer. The $R_1$ groups of this homopolymer can be exchanged off by catalytic esterification using an organic acid catalyst such as, but not limited to, p-toluene sulfonic acid in the presence of excess 1-methoxy-2-propanol. In this embodiment, it can be advantageous, but not necessary, for the $R_1$—OH alcohol so formed to be more volatile than the 1-methoxy-2-propanol (BP 119° C.) to facilitate its removal by distillation to drive the reaction. Hence, methacrylates which are esters of methanol, ethanol, n-propanol, and isopropanol are more facile to process by this scheme than, for example, poly(n-butyl methacrylate) as the n-butanol boiling point (117° C.) is very close to that of 1-methoxy-2-propanol.

In one embodiment, the copolymer compositions are manufactured to have a desired Tg when hydrated. The Tg of the copolymer can be calculated by knowing the amount of water absorbed and the Tg Tg derived from measurements of the homopolymer of the respective monomers. In an embodiment, the Tg is calculated using the Fox equation:

$$\frac{1}{T_g^{Polymer}} = \frac{W^{PC}}{T_g^{PC}} + \frac{W^{Water}}{T_g^{Water}} + \frac{W^{Methacrylate}}{T_g^{Methacrylate}}$$

where:

$T_g$ = glass transition temperature of the homopolymer or pure material $T_g^{WATER} = -40°$ C.

W = weight fraction of the components.

Once the water absorption of the polymer is known, which is usually measured experimentally, the copolymer Tg can be estimated with the desired target. In one embodiment the desired target Tg is in the range of about –30° C. to about 37° C. when in the fully hydrated state. In another range, the Tg is about 0° C. to about 37° C. when hydrated. With a Tg of less than 37° C., the copolymers of the invention will have a high degree of polymer mobility when placed in vivo. This feature allows the surface of the polymer to enrich in more MMEOA monomer content, which is advantageous for biocompatibility.

In an alternative embodiment, the copolymer is designed to have a desired Tg for the polymer in the dry state. In an embodiment, the Tg of the polymer when dry is about –30° C. to about 100° C. or about 0° C. to about 70° C.

The polymerization reaction can be controlled to produce the copolymers with a desired molecular weight. In one embodiment, the number average molecular weight of the copolymer is in the range from about 20K to about 800K; in another embodiment it is in a range from about 100K to about 600K.

In an alternative embodiment, the molecular weight of the polymer is selected to provide adhesion. In this embodiment, the molecular weight can be in the range from about 2K to about 200K. The adhesive polymer can be used on medical devices that benefit from an adhesive polymer coating.

In one embodiment, the copolymers of the invention are manufactured substantially free of cross-linking. Copolymers manufactured according to the invention can have sufficient mechanical strength when hydrated that cross-linking is not necessary for making a polymer coating suitable for coating an implantable device. The absence of cross-linking in the copolymers of the invention can give the copolymers improved elasticity, particularly when dry, which reduces the likelihood of cracking during assembly and use.

The MMEOA monomer can be made by reacting a polymerizable group with an 1-methoxy-2-propanol compound. These reactions are typically carried out suing known reaction conditions. An example of a suitable reaction for forming a 1-methoxy-2-propanol substituted monomer is:

Synthesis of MMOEM Monomer

In the forgoing reaction, 1-methoxy-2-propanol is reacted with methacryloyl chloride to yield 1-methyl-2-methoxyethyl methacrylate. 1-methoxy-2-propanol and methacryloyl chloride are commercially available compounds (e.g., 1-methoxy-2-propanol is available from the Dow Chemical Company under the product name of "Dowanol PM").

III. Use of Coatings on Medical Devices

The foregoing copolymers are suitable for use on any medical device that is compatible with polymer coatings. The copolymers can be used alone as a coating or can be combined with other polymers or agents to form a polymer coating. For example, the polymers may be blended with poly(vinyl pyrrolidinone), poly(n-butyl methacrylate), poly(n-butyl methacrylate) copolymers, methacrylate polymers, acrylate polymers, and/or a terpolymers of hexyl methacrylate, vinyl acetate, and vinyl pyrrolidinone.

The polymer coatings can be applied to a medical device using any techniques known to those skilled in the art or those that may be developed for applying a coating to a medical device. Examples of suitable techniques for applying the coating to the medical device include spraying, dip coating, roll coating, spin coating, inkjet printing, powder coating, and direct application by brush or needle. One skilled in the art will appreciate the many different techniques in powder coating. The copolymers can be applied directly to the surface of the implant device, or they can be applied over a primer or other coating material.

In one embodiment, the polymer coatings are applied to a medical device using a solvent-based technique. The polymer can be dissolved in the solvent to form a solution, which can be more easily applied to the medical device using one or more of the above mentioned techniques or another technique. Thereafter substantially all or a portion of the solvent can be removed to yield the polymer coating on a surface of the medical device.

Examples of suitable solvents that can be used with the copolymers of the invention include, but are not limited to, dimethylacetamide (DMAC), dimethylformamide (DMF), tetrahydrofuran (THF), dimethylsulfoxide (DMSO), cyclohexanone, xylene, toluene, acetone, i-propanol, methyl ethyl ketone, propylene glycol monomethyl ether, methyl t-butyl ketone, methyl isobutyl ketone, ethyl acetate, n-butyl acetate, n-butanol, ethanol, methanol, chloroform, trichloroethylene, 1,1,1-trichloroethane, methylene chloride, cyclohexane, octane, n-hexane, pentane, and dioxane. Solvent mixtures can be used as well. Representative examples of the mixtures include, but are not limited to, DMAC and methanol (50:50 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

Examples of suitable implantable devices that can be coated with the copolymers of the invention include coronary stents, peripheral stents, catheters, arterio-venous grafts, bypass grafts, pacemaker and defibrillator leads, anastomotic clips, arterial closure devices, patent foramen ovale closure devices, and drug delivery balloons. The copolymers are particularly suitable for permanently implanted medical devices.

The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel and cobalt-chromium-tungsten alloys). Suitable nonmetallic biocompatible materials include, but are not limited to, polyamides, fluoropolymers, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and the like, and combinations of these).

The copolymers are particularly advantageous as a coating for stents due to their elongation properties, which allows the coated stent to be crimped and expanded without cracking the coating. The stents can be composed of wire structures, flat perforated structures that are subsequently rolled to form tubular structures, or cylindrical structures that are woven, wrapped, drilled, etched or cut.

Figures 1A, 1B:
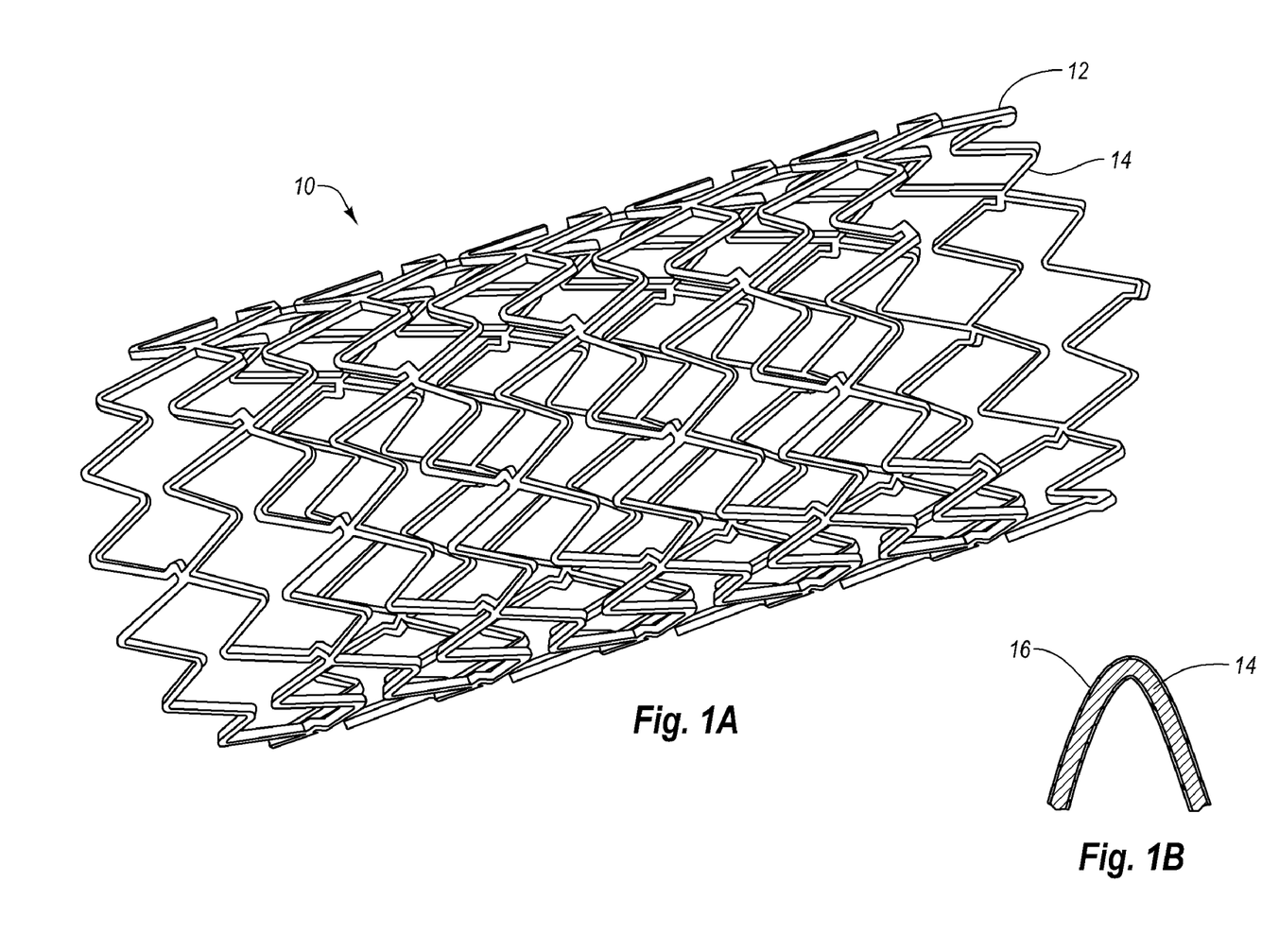
FIG. 1A illustrates an example of a stent coated with a copolymer according to one embodiment of the invention.
FIG. 1B is a cross-section of a strut of the stent of FIG. 1A.

FIG. 1A shows an example stent 10 coated with a copolymer including MMEOA monomers. Stent 10 includes a generally tubular body 12 with a lumen. The struts of body 12 (e.g. strut 14) provide a supporting structure for coating the polymers of the invention.

FIG. 1B illustrates a cross-section of the stent of FIG. 1A coated with a polymer coating 16. The polymer coating 16 can be conformal as in FIG. 1B. Alternatively, the coating can be ablumenal, luminal, or any combination thereof. In one embodiment, the copolymers of the invention are elastic at body temperatures and can therefore expand without cracking as the stent expands during use.

The polymer coated stents of the invention can be self-expanding or balloon expandable. The copolymer coatings of the invention can be particularly advantageous for self-expanding stents. Self-expanding stents are typically restrained by a sheath that is removed during deployment of the stent. The copolymers of the invention can have improved mechanical strength to better withstand the friction exerted on the polymer as the sheath is removed.

In one embodiment, a bioactive agent is associated with the coated medical devices of the invention. The bioactive agent can be associated with a base coat, top coat, mixed with the novel copolymers of the invention, and/or incorporated or otherwise applied to a supporting structure of the medical device.

The bioactive agent can have any therapeutic effect. Examples of suitable therapeutic properties include anti-proliferative, anti-inflammatory, antineoplastic, antiplatelet, anti-coagulant, anti-fibrin, antithrombonic, antimitotic, antibiotic, antiallergic and antioxidant properties.

Examples of suitable bioactive agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents, including streptokinase and tissue plasminogen activator, antigens, hormones, growth factors, ribozymes, retroviral vectors, anti-proliferative agents including rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin (zotarolimus, ABT-578), 40-epi-(N-1-tetrazolyl)-rapamycin, 40-O-[2-(2-hydroxy)ethoxy]ethyl-rapamycin, Biolimus A9 (biosensors International, Singapore), deforolimus, AP23572 (Ariad Pharmaceuticals), paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä, calcium channel blockers including nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements including vitamins, anti-inflammatory agents including aspirin, tacrolimus, dexamethasone, dexamethasone acetate, dexmethasone phosphate, momentasone, cortisone, cortisone acetate, hydrocortisone, prednisone, prednisone acetate, betamethasone, betamethasone acetate, clobetasol, cytostatic substances including angiopeptin, angiotensin converting enzyme inhibitors including captopril, cilazapril or lisinopril, antiallergic agents is permirolast potassium, alpha-interferon, bioactive RGD, and genetically engineered epithelial cells. Other bioactive agents which are currently available or that may be developed in the future for use with DESs may likewise be used and all are within the scope of this invention.

The medical devices of the invention can be used in any vascular, non-vascular, or tubular structure in the body. In an embodiment, a coated stent can be used in, but is not limited to use in, neurological, carotid, coronary, aorta, renal, biliary, ureter, iliac, femoral, and popliteal vessels.

IV. Examples

The following are specific examples of copolymers of MMEOM monomers and hydrophobic monomers. The following copolymers are useful for coating implantable medical devices.

Example 1

Example 1 describes a copolymer of poly(1-methyl-2-methoxyethyl methacrylate-co-n-butyl methacrylate) (poly (MMOEM-co-n-butyl methacrylate)). The poly(MMOEM-co-n-butylmethacrylate) has the formula:

In the foregoing formula, m is in a range from 0.25 to 0.995 and n is in a range from 0.005 to 0.75. The use of poly(n-butyl methacrylate) monomer is particularly advantageous since the homopolymer of PMBA is currently being used in implantable devices and is thus known to be biocompatible.

Example 2

Example 2 describes a copolymer of poly(1-methyl-2-methoxyethyl methacrylate-co-ethyl methacrylate))poly (MMOEM-co-ethyl methacrylate)). The chemical formula of poly (MMEOM-co-ethyl methacrylate) is:

In the foregoing formula, m is in a range from 0.25 to 0.99 and n is in a range from 0.01 to 0.75. The higher $T_g$ of the alkyl methacrylate monomer enables a harder, stronger coating at the expense of elasticity as compared to the copolymer of Example 1.

Example 3

Example 3 describes a method for manufacturing a coated stent using the polymers of Examples 1 and/or 2. In a first step, a primer coating is applied to the stent. A primer solution including between about 0.1 mass % and about 15 mass %, (e.g., about 2.0 mass %) of poly(n-butyl methacrylate) (PBMA) and the balance, a solvent mixture of acetone and cyclohexanone (having about 70 mass % of acetone and about 30 mass % of cyclohexanone) is prepared. The solution is applied onto a stent to form a primer layer.

To apply the primer layer, a spray apparatus, (e.g., Sono-Tek MicroMist spray nozzle, manufactured by Sono-Tek Corporation of Milton, N.Y.) is used. The spray apparatus is an ultrasonic atomizer with a gas entrainment stream. A syringe pump is used to supply the coating solution to the nozzle. The composition is atomized by ultrasonic energy and applied to the stent surfaces. A useful nozzle to stent distance is about 20 mm to about 40 mm at an ultrasonic power of about one watt to about two watts. During the process of applying the composition, the stent is optionally rotated about its longitudinal axis, at a speed of 100 to about 600 rpm, for example, about 400 rpm. The stent is also linearly moved along the same axis during the application.

The primer solution is applied to a 15 mm Triplex, N stent (available from Abbott Vascular Corporation) in a series of 20-second passes, to deposit, for example, 20 μg of coating per spray pass. Between the spray passes, the stent is allowed to dry for about 10 seconds to about 30 seconds at ambient temperature. Four spray passes can be applied, followed by baking the primer layer at about 80° C. for about 1 hour. As a result, a primer layer can be formed having a solids content of about 80 μg. For purposes of this invention, "Solids" means the amount of the dry residue deposited on the stent after all volatile organic compounds (e.g., the solvent) have been removed.

In a subsequent step, a copolymer solution is prepared. The copolymer solution includes the copolymer of Examples 1 and/or Example 2. The solution is prepared by dissolving between about 0.1 mass % and about 15 mass %, (e.g., about 2.0 mass %) of the copolymer in a solvent. The solvent can be a mixture of about 70 mass % acetone and about 30 mass % cyclohexanone.

In a manner similar to the application of the primer layer, the copolymer solution is applied to a stent. Twenty spray passes are performed with a coating application of 10 ug per pass, with a drying time between passes of 10 seconds, followed by baking the copolymer layer at about 60° C. for about 1 hour, to form a layer having a solids content between about 30 μg and 750 μg, (e.g., about 200 μg).

Example 4

Example 4 describes a method for manufacturing a drug eluting stent according to the invention. The medical device is manufactured using the same method as in Example 3, except that instead of the copolymer solution, a polymer-therapeutic solution is prepared and applied using the following formula.

A drug-including formulation is prepared that includes:
(a) between about 0.1 mass % and about 15 mass %, (e.g., about 2.0 mass %) of the copolymer of Example 1 and/or Example 2;
(b) between about 0.1 mass % and about 2 mass %, for example, about 1.0 mass % of a therapeutic agent. In one embodiment, the therapeutic agent is ABT-578 (available from Abbott Vascular Corp. of Chicago, Ill.); and
(c) the balance, a solvent mixture including about 70 mass % of acetone and about 30 mass % of cyclohexanone.

The drug-including formulation is applied to the stent in a manner similar to the application of the copolymer solution in Example 3. The process results in the formation of a drug-polymer reservoir layer having a solids content between about 30 μg and 750 μg, (e.g., about 200 μg), and a drug content of between about 10 μg and about 250 μg, (e.g., about 67 μg).

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Recitation of ranges of values herein are merely intended to serve as a shorthand method of referring individually to each separate value falling within the range, unless otherwise indicated herein, and each separate value is incorporated into the specification as if it were individually recited herein.

What is claimed is:
1. A method for manufacturing a biocompatible copolymer, comprising:
polymerizing a plurality of acrylate monomers to yield a copolymer having the following formula, in which,
R₁ is a straight chain, branched, unsaturated or cyclic hydrocarbon of one to sixteen carbons;
R₂ and R₃ are independently a hydrogen or a methyl group,
m is in a range of from 0.1 to 0.995; and
n is in a range from 0.005 to 0.9,
wherein the plurality of acrylate monomers are polymerized to form an intermediate polymer and a 1-methyl-2-methoxyethyl group is thereafter coupled to the intermediate polymer, which is the polymer corresponding to the repeating portion subscripted "m" or R₁ group is thereafter coupled to the intermediate polymer, which is the polymer corresponding to the repeating portion subscripted "n," to yield the copolymer.

2. A method as in claim 1, in which the copolymer is formed by reacting a hydrophobic monomer with a 1-methyl-2-methoxyethyl acrylate monomer.

3. A method as in claim 1, in which the R₁ group is coupled to an acrylate monomer of the intermediate polymer.

4. A method as in claim 3, in which the coupling of the R₁ group to the intermediate polymer is carried out by a transesterification process in which an ester bond is formed between a hydrophobic compound and an acrylate monomer of the intermediate polymer.

5. A method as in claim 1, in which the 1-methoxy-2-methoxyethyl group is coupled to an acrylate monomer of the intermediate polymer.

6. A method as in claim 5, in which the coupling of the 1-methyl-2-methoxyethyl group to the intermediate polymer is carried out by a transesterification process in which an ester bond is formed between a 1-methoxy-2-propanol and an acrylate monomer of the intermediate polymer.

7. A method as in claim 1, in which R₁ is selected from the group consisting of methyl, ethyl, n-propyl, isopropyl, n-butyl, isobutyl, sec-butyl, 2-ethyl-hexyl, n-hexyl, cyclohexyl, n-hexyl, isobornyl, trimethylcyclohexyl and combination thereof.

8. A method as in claim 1, further comprising forming the 1-methyl-2-methoxyethyl acrylate monomer by reacting a polymerizable compound with 1-methoxy-2-propanol to yield the 1-methyl-2-methoxyethyl acrylate monomer.

9. A method as in claim 2, in which the concentration of the hydrophobic monomer and the concentration of the 1-methyl-2-methoxyethyl acrylate monomer are selected to yield a thermoplastic polymer with a hydrated glass transition temperature in a range from about −30° C. to about 37° C.

10. A method as in claim 2, in which the concentration of the hydrophobic monomer and the concentration of the 1-methyl-2-methoxyethyl acrylate monomer are selected to yield a thermoplastic polymer with a hydrated glass transition temperature in a range from about 0° C. to about 37° C.

11. A method as in claim 2, in which the concentration of the hydrophobic monomer and the concentration of the 1-methyl-2-methoxyethyl acrylate monomer are selected to yield a thermoplastic polymer with a dry glass transition temperature in a range from about −30° C. to about 100° C.

12. A method as in claim 2, in which the concentration of the hydrophobic monomer and the concentration of the 1-methyl-2-methoxyethyl acrylate monomer are selected to yield a thermoplastic polymer with a dry glass transition temperature in a range from about 0° C. to about 70° C.

13. A method as in claim 1, in which the copolymer has a number average molecular weight in a range from about 20K to about 800K.

14. A method as in claim 1, in which the copolymer has a number average molecular weight in a range from about 100K to about 600K.

15. A method as in claim 1, in which the copolymer has a number average molecular weight in a range from about 2K to about 200K.

16. A method as in claim 1, in which the copolymerization reaction is carried out using free radical polymerization, atom transfer radical polymerization, cationic polymerization, anionic polymerization, or iniferter polymerization.

* * * * *